(12) United States Patent
Hashimoto et al.

(10) Patent No.: US 10,792,114 B2
(45) Date of Patent: Oct. 6, 2020

(54) REMOTE CONTROL ROBOT SYSTEM AND METHOD OF OPERATING THE SAME

(71) Applicant: KAWASAKI JUKOGYO KABUSHIKI KAISHA, Kobe-shi, Hyogo (JP)

(72) Inventors: Yasuhiko Hashimoto, Kobe (JP);
Nobuyasu Shimomura, Kobe (JP);
Masayuki Kamon, Akashi (JP);
Yasushi Kurosawa, Kakogawa (JP);
Shigetsugu Tanaka, Akashi (JP)

(73) Assignee: KAWASAKI JUKOGYO KABUSHIKI KAISHA, Kobe-shi (JP)

( * ) Notice: Subject to any disclaimer, the term of this patent is extended or adjusted under 35 U.S.C. 154(b) by 251 days.

(21) Appl. No.: 15/755,105

(22) PCT Filed: May 27, 2016

(86) PCT No.: PCT/JP2016/002574
§ 371 (c)(1),
(2) Date: Feb. 26, 2018

(87) PCT Pub. No.: WO2017/033350
PCT Pub. Date: Mar. 2, 2017

(65) Prior Publication Data
US 2018/0243910 A1    Aug. 30, 2018

(30) Foreign Application Priority Data
Aug. 25, 2015 (JP) ................................ 2015-165479

(51) Int. Cl.
*A61B 34/37* (2016.01)
*B25J 9/00* (2006.01)
(Continued)

(52) U.S. Cl.
CPC ............... *A61B 34/37* (2016.02); *A61B 34/32* (2016.02); *B23P 19/04* (2013.01); *B23Q 15/12* (2013.01);
(Continued)

(58) Field of Classification Search
CPC ......... A61B 34/37; A61B 34/32; A61B 34/35; A61B 34/70; G05B 19/4182; G06T 7/62;
(Continued)

(56) References Cited

U.S. PATENT DOCUMENTS 4,837,734 A    6/1989    Ichikawa et al.
5,136,223 A    8/1992    Karakama et al.
(Continued)

FOREIGN PATENT DOCUMENTS

JP    H08-5018 A    1/1996
JP    2003-311661 A    11/2003
(Continued)

OTHER PUBLICATIONS

May 17, 2019 Extended European Search Report issued in European Patent Application No. 16838702.5.

*Primary Examiner* — Jaime Figueroa
(74) *Attorney, Agent, or Firm* — Oliff PLC (57) ABSTRACT

In a remote control robot system including a plurality of slave arms, slave arm has a plurality of control modes of an automatic mode in which slave arm is operated based on a task program, a manual mode in which slave arm is operated based on an operator's operation received by a master device, and correctable automatic mode in which slave arm is operated based on task program while operation is sequentially corrected by the operator's operation received by master device. Operation sequence information includes an automatic part in which slave arm performs a work in the automatic mode, and a selected part in which slave arm (Continued)

performs a work in one selected from plurality of control modes, and the selected parts do not overlap with each other in time among the plurality of slave arms. Based on the operation sequence information, the plurality of slave arms are operated.

8 Claims, 4 Drawing Sheets

(51) Int. Cl.
| | |
|---|---|
| A61B 34/32 | (2016.01) |
| G06T 7/70 | (2017.01) |
| B25J 9/16 | (2006.01) |
| G05B 19/418 | (2006.01) |
| B23P 19/04 | (2006.01) |
| B25J 13/00 | (2006.01) |
| B25J 19/04 | (2006.01) |
| B25J 13/08 | (2006.01) |
| B25J 3/00 | (2006.01) |
| B25J 13/06 | (2006.01) |
| B25J 18/00 | (2006.01) |
| B25J 19/02 | (2006.01) |
| B25J 3/04 | (2006.01) |
| B23Q 15/12 | (2006.01) |
| B25J 13/02 | (2006.01) |
| B25J 11/00 | (2006.01) |
| G06F 3/01 | (2006.01) |
| H04N 5/232 | (2006.01) |
| H04N 7/18 | (2006.01) |
| G06T 7/62 | (2017.01) |
| B23P 21/00 | (2006.01) |

(52) U.S. Cl.
CPC . *B25J 3/00* (2013.01); *B25J 3/04* (2013.01); *B25J 9/0081* (2013.01); *B25J 9/0084* (2013.01); *B25J 9/0087* (2013.01); *B25J 9/161* (2013.01); *B25J 9/1602* (2013.01); *B25J 9/163* (2013.01); *B25J 9/1612* (2013.01); *B25J 9/1628* (2013.01); *B25J 9/1633* (2013.01); *B25J 9/1646* (2013.01); *B25J 9/1653* (2013.01); *B25J 9/1664* (2013.01); *B25J 9/1669* (2013.01); *B25J 9/1674* (2013.01); *B25J 9/1682* (2013.01); *B25J 9/1689* (2013.01); *B25J 9/1697* (2013.01); *B25J 11/008* (2013.01); *B25J 13/00* (2013.01); *B25J 13/003* (2013.01); *B25J 13/006* (2013.01); *B25J 13/02* (2013.01); *B25J 13/025* (2013.01); *B25J 13/06* (2013.01); *B25J 13/065* (2013.01); *B25J 13/08* (2013.01); *B25J 13/084* (2013.01); *B25J 13/085* (2013.01); *B25J 13/087* (2013.01); *B25J 13/088* (2013.01); *B25J 18/00* (2013.01); *B25J 19/023* (2013.01); *B25J 19/028* (2013.01); *B25J 19/04* (2013.01); *G05B 19/4182* (2013.01); *G06F 3/017* (2013.01); *G06T 7/62* (2017.01); *G06T 7/70* (2017.01); *H04N 5/23219* (2013.01); *H04N 7/181* (2013.01); *B23P 21/00* (2013.01); *B23P 21/002* (2013.01); *G05B 2219/33007* (2013.01); *G05B 2219/35464* (2013.01); *G05B 2219/37297* (2013.01); *G05B 2219/39004* (2013.01); *G05B 2219/39102* (2013.01); *G05B 2219/39439* (2013.01); *G05B 2219/39531* (2013.01); *G05B 2219/39533* (2013.01); *G05B 2219/40022* (2013.01); *G05B 2219/40134* (2013.01); *G05B 2219/40136* (2013.01); *G05B 2219/40139* (2013.01); *G05B 2219/40142* (2013.01); *G05B 2219/40143* (2013.01); *G05B 2219/40145* (2013.01); *G05B 2219/40146* (2013.01); *G05B 2219/40161* (2013.01); *G05B 2219/40162* (2013.01); *G05B 2219/40163* (2013.01); *G05B 2219/40169* (2013.01); *G05B 2219/40182* (2013.01); *G05B 2219/40183* (2013.01); *G05B 2219/40195* (2013.01); *G05B 2219/40387* (2013.01); *G05B 2219/40627* (2013.01); *Y10S 901/02* (2013.01); *Y10S 901/03* (2013.01); *Y10S 901/08* (2013.01); *Y10S 901/09* (2013.01); *Y10S 901/10* (2013.01); *Y10S 901/27* (2013.01); *Y10S 901/41* (2013.01); *Y10S 901/46* (2013.01); *Y10S 901/47* (2013.01)

(58) Field of Classification Search
CPC ......... G06T 7/70; B25J 9/0081; B25J 9/1612; B25J 13/006; B25J 3/00; B25J 13/06; B25J 13/02; G06F 3/017
USPC .................................................. 700/245, 264
See application file for complete search history.

(56) References Cited

U.S. PATENT DOCUMENTS

| | | | | |
|---|---|---|---|---|
| 5,404,290 | A * | 4/1995 | Tsuchihashi | B25J 9/1674 |
| | | | | 700/61 |
| 5,808,665 | A | 9/1998 | Green | |
| 6,241,704 | B1* | 6/2001 | Peterson | A61M 5/14228 |
| | | | | 604/65 |
| 9,333,042 | B2* | 5/2016 | Diolaiti | A61B 34/37 |
| 9,469,034 | B2* | 10/2016 | Diolaiti | A61B 1/00087 |
| 9,789,603 | B2* | 10/2017 | Jacobsen | B25J 13/025 |
| 9,795,446 | B2* | 10/2017 | DiMaio | A61B 34/10 |
| 2003/0167238 | A1* | 9/2003 | Zeif | G05B 23/0267 |
| | | | | 705/400 |
| 2004/0254680 | A1* | 12/2004 | Sunaoshi | A61B 34/70 |
| | | | | 700/253 |
| 2005/0166413 | A1* | 8/2005 | Crampton | B25J 13/088 |
| | | | | 33/503 |
| 2006/0095143 | A1* | 5/2006 | Sunaoshi | B25J 9/1689 |
| | | | | 700/3 |
| 2009/0119437 | A1* | 5/2009 | Hilscher | H04L 12/407 |
| | | | | 710/305 |
| 2011/0238079 | A1* | 9/2011 | Hannaford | G06F 3/011 |
| | | | | 606/130 |
| 2011/0306986 | A1 | 12/2011 | Lee et al. | |
| 2012/0328395 | A1* | 12/2012 | Jacobsen | B25J 13/025 |
| | | | | 414/1 |
| 2014/0039681 | A1 | 2/2014 | Bowling et al. | |
| 2015/0224639 | A1* | 8/2015 | Dockter | B25J 3/04 |
| | | | | 700/264 |

FOREIGN PATENT DOCUMENTS

| | | |
|---|---|---|
| WO | 2010/110560 A2 | 9/2010 |
| WO | 2014/151550 A2 | 9/2014 |

\* cited by examiner

REMOTE CONTROL ROBOT SYSTEM AND METHOD OF OPERATING THE SAME

TECHNICAL FIELD

The present disclosure relates to a remote control robot system provided with a master device and a slave arm, and a method of operating the remote control robot system.

BACKGROUND ART

Conventionally, remote control robot systems provided with a master device (i.e., a remote control device) and a slave arm which operates according to operation of the master device are known. As the master device, a manipulator, a control lever, an operating button, etc. may be used. In such remote control robot systems, some of them are configured so that the posture of the slave arm is made to follow the posture of a robotic arm as the master device, and a reaction force acting on the slave arm is transmitted to an operator through the master device. Such a kind of technology is disclosed in Patent Document 1.

Patent Document 1 discloses a remote control robot system having three operating modes of an automatic operating mode, a manual operating mode, and a manual operating mode with restraint which assists a manual operation, such as restraining to a hand posture by a slave operation managing means, and switches the operating mode according to a work sequence plan. In the automatic operating mode, the slave operation managing means causes the slave arm to execute a work in accordance with a given program. Moreover, in the manual operating mode and the manual operating mode with restraint, mainly, an interface means causes the slave arm to execute a work according to operation inputted into the master device by an operator. In addition, in the manual operating mode with restraint, the slave operation managing means executes operation which assists the operation.

Moreover, in the remote control robot system disclosed in Patent Document 1, a remote control method is disclosed, which includes creating a work sequence plan in which a manual operation part and an automatic operation part are mixed based on data indicative of the operator's skill and a given work objective, operates the system in the automatic operating mode for the automatic operation part of the work sequence plan, and operates the system in the manual operating mode or the manual operating mode with restraint for the manual operation part of the work sequence plan.

REFERENCE DOCUMENT OF CONVENTIONAL ART

Patent Document

DESCRIPTION OF THE DISCLOSURE

Problems to be Solved by the Disclosure

In the technology of Patent Document 1, when the mode is switched to the manual operating mode or the manual operating mode with restraint, the slave operation managing means does not use the program which is used in the automatic operating mode. Thus, in the manual operating mode or the manual operating mode with restraint, an operator's load becomes excessive and the work efficiency is lowered.

Moreover, although Patent Document 1 describes that the remote control robot system may be provided with a plurality of slave arms, it is based on the assumption that the rate of the automatic operation is large. Thus, when the remote control robot system is provided with the plurality of slave arms, the operations of the slave arms may differ from each other, and the operator's load may become remarkably excessive. Therefore, the room of improvement is left behind in the technology of Patent Document 1 for performing an efficient work using the plurality of slave arms.

SUMMARY OF THE DISCLOSURE

According to one aspect of the present disclosure, a method of operating a remote control robot system provided with a master device and a plurality of slave arms is provided. Each of the slave arms has a plurality of control modes of an automatic mode in which the slave arm is operated based on a prestored task program, a manual mode in which the slave arm is operated based on an operator's operation received by the master device, and a correctable automatic mode in which the slave arm is operated based on the task program while the operation is sequentially corrected by an operator's operation received by the master device. The method includes a step of creating operation sequence information that includes an automatic part in which the slave arm performs a work in the automatic mode, and a selected part in which the slave arm performs a work in one selected from the plurality of control modes, and the selected parts do not overlap with each other in time among the plurality of the slave arms, and a step of the slave arm performing the work based on the operation sequence information, by operating the slave arm in the automatic mode in the automatic part, and operating the slave arm in the control mode that is selected from the plurality of control modes for every selected part in the selected part.

According to another aspect of the present disclosure, a remote control robot system is provided, which includes a master device configured to receive an operator's operation, a plurality of slave arms having a plurality of control modes of an automatic mode in which the slave arm is operated based on a prestored task program, a manual mode in which the slave arm is operated based on the operator's operation received by the master device, and a correctable automatic mode in which the slave arm is operated based on the task program while the operation is sequentially corrected by the operator's operation received by the master device, a storage device configured to store operation sequence information that includes an automatic part in which the slave arm performs a work in the automatic mode, and a selected part in which the slave arm performs a work in one selected from the plurality of control modes, and the selected parts do not overlap with each other in time among the plurality of slave arms, and the task program, and a slave control device configured to cause the slave arm, based on the operation sequence information, to operate in the automatic mode in the automatic part, and to operate the slave arm in the control mode that is selected from the plurality of control modes for every selected part in the selected part.

According to the remote control robot system and the method of operating the same described above, the control mode of the slave arm is able to be selected from the automatic mode, the manual mode, and the correctable automatic mode according to the contents of work or a status of the slave arm. The selection of the control mode can be performed by the judgment of the operator. For example, when occurring of a failure is expected if the slave arm is completely operated automatically, the slave arm may be operated in the correctable automatic mode. In the correctable automatic mode, since the automatic operation of the slave arm is used as the basis, and the operation is correctable by the operator's operation, the operator's load is less and a reduction of the work efficiency is suppressed, as compared with the manual mode. Thus, a nonstop robot system is achieved by the operator selecting the control mode suitable for the status from the plurality of control modes.

Moreover, the manual mode and the correctable automatic mode which require the operator's operation do not appear simultaneously in the plurality of slave arms. Therefore, the operator remotely operates the plurality of slave arms with one master device, and idle times of the slave arm and the operator are shortened. Thus, the efficient work can be performed using the plurality of slave arms.

Effect of the Disclosure

According to the remote control robot system and the method of operating the same of the present disclosure, the efficient work can be performed using the plurality of slave arms.

MODES FOR CARRYING OUT THE DISCLOSURE

Hereinafter, one embodiment of the present disclosure is described with reference to the accompanying drawings.

Remote Control Robot System 100

Figure 1:
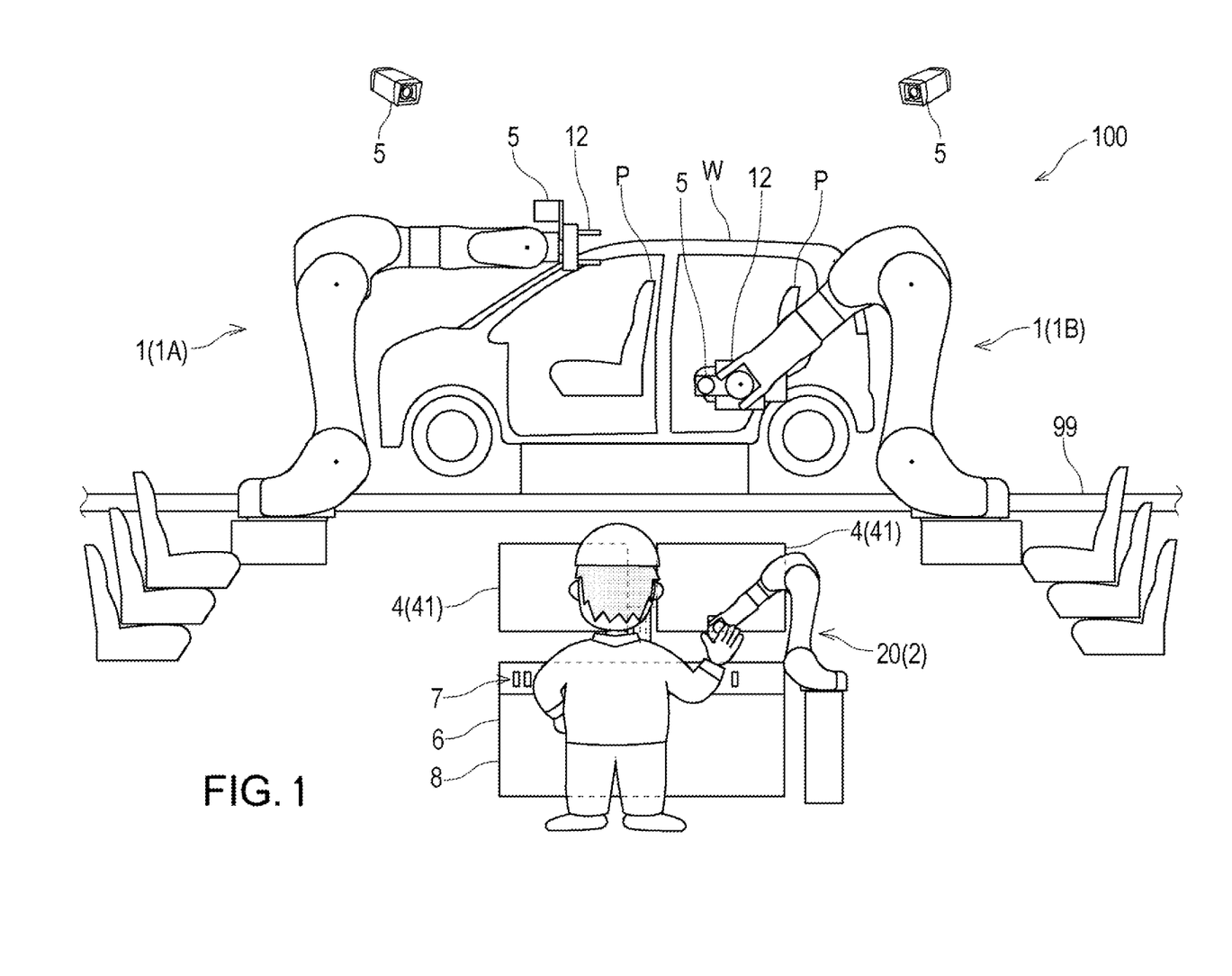
FIG. 1 is a view illustrating an appearance of an automobile assembly line into which a remote control robot system according to one embodiment of the present disclosure is introduced.
Figure 2:
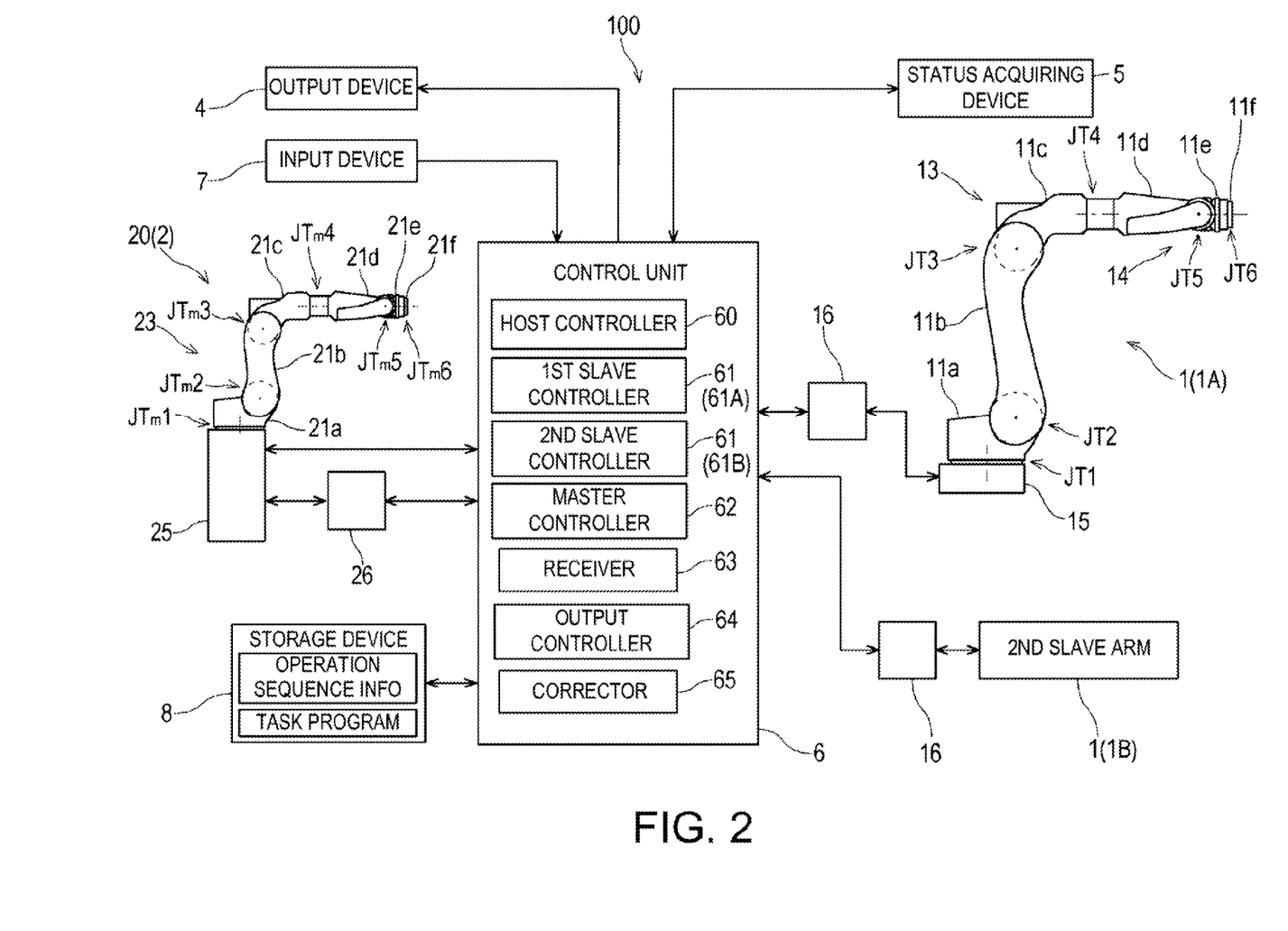
FIG. 2 is a block diagram schematically illustrating a configuration of the remote control robot system.

FIG. 1 is a view illustrating an appearance of an automobile assembly line provided with a remote control robot system 100 according to one embodiment of the present disclosure, and FIG. 2 is a block diagram schematically illustrating a configuration of the remote control robot system 100. As illustrated in FIGS. 1 and 2, the remote control robot system 100 is a master-slave type robot system, and includes a plurality of slave arms 1 (1A and 1B), a master device 20, an input device 7, an output device 4, a status acquiring device 5, and a control unit 6 which comprehensively controls the system 100. Herein, when not distinguishing the plurality of slave arms 1A and 1B, A or B of the alphabet attached to the number of 1 is omitted and it is simply expressed as "the slave arm 1."

In FIG. 1, illustrated is the automobile assembly line provided with a conveyor line of a workpiece W, which is formed by a conveyor 99 in a workspace, the plurality of slave arms 1A and 1B installed along the conveyor line, and the master device 20 installed at a position distant from the workspace (outside of the workspace). In this automobile assembly line, the slave arm 1 is capable of performing a work, such as transferring of the workpiece W, assembling and relocating of a component, posture conversion, and painting. Note that the remote control robot system 100 according to the present disclosure is not limited to such an automobile assembly line, but may be applicable widely to various production facilities.

The slave arm 1 according to this embodiment has three control modes of an automatic mode, a manual mode, and a correctable automatic mode. The control mode of the slave arm 1 can be switched so that operation is controlled in one selected from the plurality of control modes.

The control mode in which the slave arm 1 is operated according to a preset task program is herein referred to as "the automatic mode." In the automatic mode, the slave arm 1 automatically performs a given work without the operation of the master device 20 by an operator, similar to a conventional teaching playback robot.

Moreover, the control mode in which the slave arm 1 is operated based on the operator's operation received by the master device 20 is herein referred to as "the manual mode." The master device 20 is capable of receiving operation inputted by the operator directly operating the master device 20. Note that, in the manual mode, the operator's operation received by the master device 20, and/or the motion of the slave arm 1 which is operated based on the operation may be corrected automatically.

Moreover, the control mode in which the slave arm 1 is operated according to the preset task program while the operation is sequentially corrected according to the operator's operation received by the master device 20 is herein referred to as "the correctable automatic mode." In the correctable automatic mode, the motion of the slave arm 1 which is operated according to the preset task program is corrected based on the operator's operation received by the master device 20.

Below, each element of the remote control robot system 100 is described in detail.

Slave Arm 1

In FIG. 1, two slave arms 1 of the first slave arm 1A and the second slave arm 1B, which are installed so as to be separated from each other in parallel to the conveyor line of the workpiece W, are illustrated. The two slave arms 1 are vertical articulated robots, and have substantially the same structure except for end effectors 12. Note that the forms of the plurality of slave arms 1 provided to the remote control robot system 100 are not limited to this embodiment, but each slave arm 1 may be a horizontal or vertical articulated robotic arm (manipulator) having three or more joints (axes). Moreover, the plurality of slave arms 1 may include multiple kinds of robotic arms having different link lengths and different number of joints.

As illustrated in FIG. 2, the slave arm 1 is an articulated robotic arm having a plurality of joints JT1-JT6, which is comprised of a serially-connected body of a plurality of links 11a-11f and a pedestal 15 which supports the serially-connected body. In more detail, in the first joint JT1, the pedestal 15 is coupled to a base-end part of the first link 11a so as to be rotatable about an axis extending in the vertical directions. In the second joint JT2, a tip-end part of the first link 11a is coupled to a base-end part of the second link 11b so as to be rotatable about an axis extending in horizontal directions. In the third joint JT3, a tip-end part of the second link 11b is rotatably coupled to the base-end part of the third link 11c about an axis extending in horizontal directions. In the fourth joint JT4, a tip-end part of the third link 11c is rotatably coupled to a base-end part of the fourth link 11d about an axis extending in the longitudinal directions of the fourth link 11d. In the fifth joint JT5, a tip-end part of the fourth link 11d is rotatably coupled to a base-end part of the fifth link 11e about an axis perpendicular to the longitudinal directions of the fourth link 11d. In the sixth joint JT6, a tip-end part of the fifth link 11e is coupled to a base-end part of the sixth link 11f so as to be twistable. A mechanical interface is provided to a tip-end part of the sixth link 11f. The end effector 12 (see FIG. 1) corresponding to the contents of work is attachably and detachably mounted to the mechanical interface.

An arm part 13 of the slave arm 1 is formed with the connected body of the links and joints, which is comprised of the first joint JT1, the first link 11a, the second joint JT2, the second link 11b, the third joint JT3, and the third link 11c, which are described above. Moreover, a wrist part 14 of the slave arm 1 is formed with the connected body of the links and joints, which is comprised of the fourth joint JT4, the fourth link 11d, the fifth joint JT5, the fifth link 11e, the sixth joint JT6, and the sixth link 11f, which are described above. The arm part 13 takes the role of positioning the end effector 12, and the wrist part 14 takes the role of orientating the end effector 12.

Figure 3:
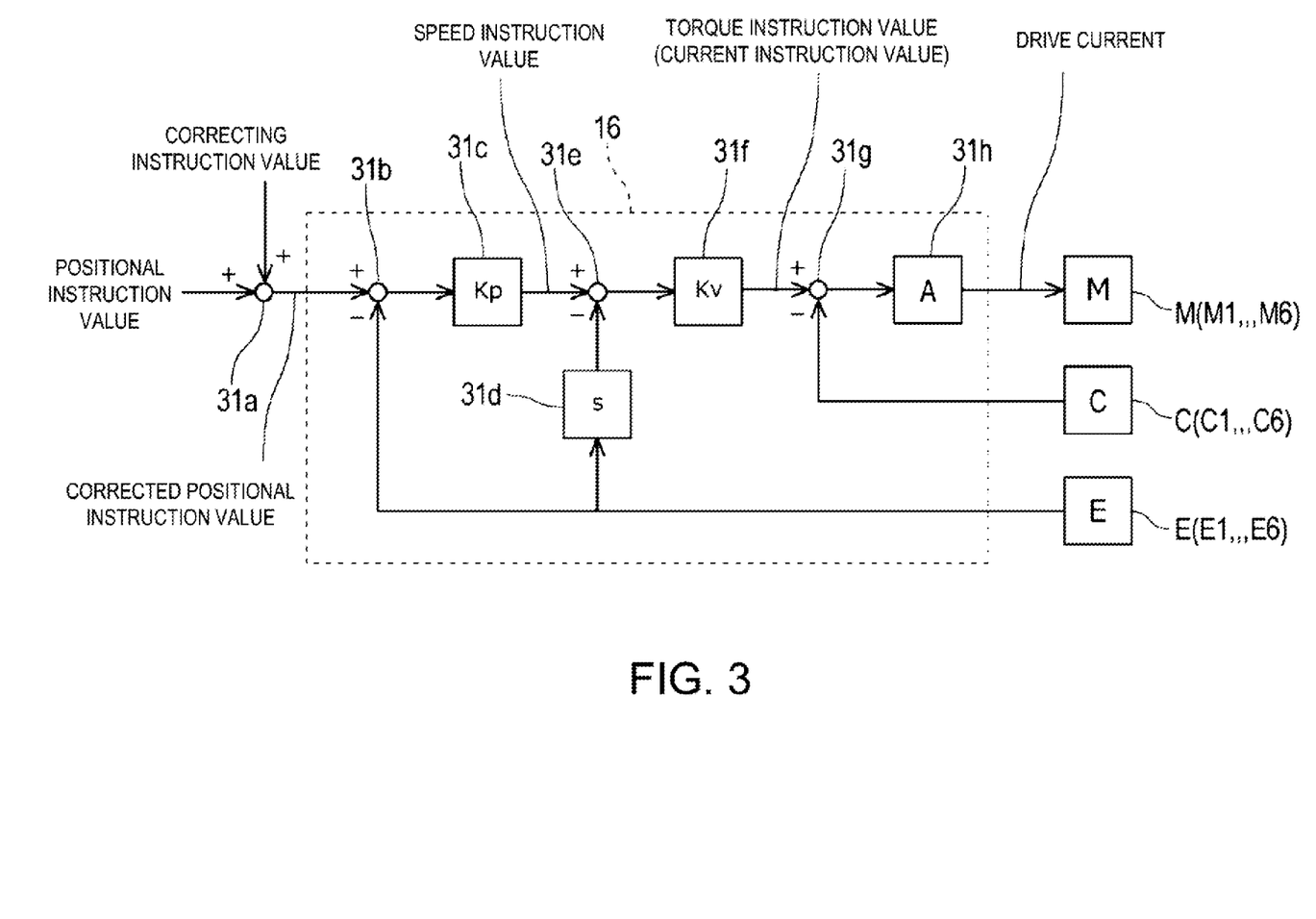
FIG. 3 is a block diagram illustrating a configuration of a control system of a slave arm.

FIG. 3 is a block diagram illustrating a configuration of a control system of the slave arm 1. In this figure, a concrete electric configuration is illustrated, focusing on a motor controller 16. As illustrated in FIG. 3, drive motors M1-M6 are provided to the respective joints JT1-JT6 of the slave arm 1, as one example of actuators, each of which relatively rotates two members connected by the joint. The drive motors M1-M6 are, for example, servo motors which are servo-controlled by the motor controller 16. Moreover, the drive motors M1-M6 are provided with position sensors E1-E6 for detecting a rotational position thereof and current sensors C1-C6 for detecting current which controls the rotation, respectively. The position sensors E1-E6 may be sensors which is capable of detecting the rotational position, such as encoders, resolvers, or pulse generators. Note that, in the description of the drive motors M1-M6, the position sensors E1-E6, and the current sensors C1-C6, suffixes 1-6 are given to the alphabet corresponding to the respective joints JT1-JT6. Below, when an arbitrary joint is illustrated out of the joints JT1-JT6, the joint is referred to as "JT" while omitting the suffix, and the same is applied to the drive motor M, the position sensor E, and the current sensor C.

The drive motors M, the position sensors E, and the current sensors C are electrically coupled to the motor controller 16. Although the motor controller 16 according to this embodiment is capable of servo-controlling the plurality of drive motors M alone, motor controllers may be provided corresponding to the respective drive motors M.

The motor controller 16 generates a drive instruction value (current instruction value) based on a positional instruction value, a servo gain, etc. which are acquired from the control unit 6 (in detail, a slave controller 61) described later, and supplies drive current corresponding to the drive instruction value to the drive motor M. An output rotational angle of the drive motor M is detected by the position sensor E, and is fed back to the motor controller 16. Note that the functions of the motor controller 16 and the slave controller 61 may be implemented by a single circuit or a single arithmetic device.

When the positional instruction value is inputted into the motor controller 16 from the control unit 6 (in detail, the slave controller 61), the inputted positional instruction value is given to a plus-side input of a subtractor 31b. A signal indicative of the rotational angle detected by the position sensor E (present positional value) is given to a minus-side input of the subtractor 31b. The subtractor 31b subtracts the rotational angle from the positional instruction value. The output of the subtractor 31b is given to a scale multiplier 31c where the output is amplified by a position gain Kp, and is then given to a plus-side input of a subtractor 31e. To a minus-side input of the subtractor 31e, a signal obtained by differentiating the rotational angle from the position sensor E in a differentiator 31d is given. The output of the subtractor 31e is given to a scale multiplier 31f where the output is amplified by a speed gain K, and it is given to a plus-side input of a subtractor 31g. The current value from the current sensor C is given to a minus-side input of the subtractor 31g. The subtracted output of the subtractor 31g is inputted into an amplifier circuit 31h as the drive instruction value, and the drive current corresponding to the amplified drive instruction value is supplied to the drive motor M.

Master Device 20

The master device 20 is a means for receiving an operator's operation. The master device 20 of the remote control robot system 100 according to this embodiment is a master arm 2, i.e., an articulated robotic arm (manipulator), and the system 100 is built so that the slave arm 1 operates so as to follow the motion of the master arm 2. That is, the master arm 2 is configured so that the position and posture of the slave arm 1 are instinctively operable.

The master arm 2 is an articulated robotic arm having a plurality of joints JTm1-JTm6, of which the number is the same as that of the slave arm 1, and is constructed by serially coupling a pedestal 25 and a plurality of links 21a-21f. The serially coupling structure of the links 21a-21f of the master arm 2 is substantially the same as that of the links 11a-11f of the slave arm 1 and, thus, detailed description thereof is omitted. A pseudo end effector which has a similarity to or corresponds to the end effector 12 attached to the slave arm 1 may be attached to the tip-end part of the sixth link 21f of the master arm 2.

Drive motors Mm1-Mm6 (not illustrated) are provided to the joints JTm1-JTm6, respectively, as one example of the actuator which relatively rotates the two components connected by the joint. The drive motors Mm1-Mm6 are, for example, servo motors which are servo-controlled by a motor controller 26. Moreover, the drive motors Mm1-Mm6 are provided with position sensors Em1-Em6 (not illustrated) for detecting rotational positions thereof and current sensors Cm1-Cm6 (not illustrated) for detecting current which controls the rotations. The position sensors Em1-Em6 are, for example, encoders. Note that, in the description of the drive motors Mm1-Mm6, the position sensors Em1-Em6, and the current sensors Cm1-Cm6, suffixes 1-6 are given to the alphabet corresponding to the respective joints JTm1-JTm6. Below, when an arbitrary joint is illustrated out of the joints JTm1-JTm6, the joint is referred to as "JTm" while omitting the suffix, and the same is applied to the drive motor Mm, the position sensor Em, and the current sensor Cm.

Similar to the drive system of the slave arm 1, the drive motor Mm, the position sensor Em, and the current sensor Cm are electrically coupled to the motor controller 26. Although the motor controller 26 according to this embodiment is capable of servo-controlling the plurality of drive motors Mm alone, motor controllers may be provided corresponding to the respective drive motors Mm.

Similar to the motor controller 16, the motor controller 26 generates a drive instruction value (torque instruction value) based on a positional instruction value, a servo gain, etc. which are acquired from the control unit 6 (in detail, a master controller 62) described later, and supplies drive current corresponding to the drive instruction value to the drive motor Mm. The output rotational angle of the drive motor Mm is detected by the position sensor Em, and is fed back to the motor controller 26. Note that the functions of the motor controller 26 and the master controller 62 may be implemented by a single circuit or a single arithmetic device.

The slave arm 1 and the master arm 2 are articulated robotic arms with the same number of axes, but their link length ratios of the arm parts 13 and 23 are different. That is, the slave arm 1 and the master arm 2 may not have similar shapes. Note that, the link length of the link is a distance from the joint of the link on the base-end side to the joint on the tip-end side. The slave arm 1 and the master arm 2 according to this embodiment are 6-axes robotic arms, and the links which form the arm parts 13 and 23 are first to third links. Although, as the slave arm 1, one having the arm part 13 of a suitable link length ratio for the contents of work or the target workpiece is introduced into the system 100, while, as the master arm 2, one having the arm part 23 of a link length ratio which is easy to be handled by the operator is adopted. For example, when the link length ratio of the first link 11a, the second link 11b, and the third link 11c of the slave arm 1 is 1:4:2, the link length ratio of the first link 21a, the second link 21b, and the third link 21c of the master arm 2 may be 1:2:2.

Input Device 7

The input device 7 is an input means, which is installed outside the workspace together with the master arm 2, receives an operating instruction from the operator, and inputs the received operating instruction into the control unit 6. Into the input device 7, operations other than operation according to the position and posture of the slave arm 1 are inputted. One or more operational input tools, such as an operational input tool for selecting the control mode of the slave arm 1, and an emergency stop switch, which input operational instructions other than the position and posture of the slave arms 1 are provided to the input device 7. The one or more operational input tools may include, for example, known operational input tools, such as a touch panel, a key, a lever, a button, a switch, and a dial plate. Alternatively, a mobile terminal, such as a programmable display device (pendant) and a tablet computer, may be used as the input device 7.

Status Acquiring Device 5

The status acquiring device 5 is a means for acquiring the status information indicative of the status of each slave arm 1 in the workspace. The status information includes information utilized in order to recognize the position, the posture, etc. of the slave arm 1 in the workspace or the status around the slave arm 1. More specifically, the status information includes, for example, information required in order to enable the recognition of the status of the slave arm 1 and the status around the slave arm 1 in the workspaces, such as the position and posture of the slave arm 1 in the workspace, a spatial relationship between the slave arm 1 and the workpiece, or a spatial relationship between the slave arm 1 and an assembled component to which the workpiece is assembled.

The status acquiring device 5 is implementable by, for example, an imaging device, such as a sensor or a camera, a communication device, an encoder, etc. The sensor may include, for example, a laser sensor, a radar sensor or the like for measuring the distance to or the position of an assembling component or the assembled component. Further, the sensor may include a stereoscopic camera which is a sensor for measuring the distance from the slave arm 1 to an object therearound by using image data obtained from a plurality of imaging devices. The communication device may include, for example, a communication device which acquires information from the assembling component or the assembled component, or a sensor and an imaging device installed at given positions in the workspace. The encoder may include, for example, an encoder capable of detecting an amount of movement or the position of the slave arm 1.

The status acquiring device 5 sequentially acquires the status information, the acquired status information is inputted into the control unit 6 described later, and the information is used for the motion control of the slave arm 1 in the control unit 6. Further, the control unit 6 may be configured to control the output device 4 to output the status information. The status acquiring device 5 may be attached to slave arm 1 itself, or may be attached to a suitable position in the workspace. Moreover, the number of status acquiring devices 5 to be attached may be one, or may be more. A suitable number of the status acquiring devices 5 may be attached at positions where they can appropriately acquire the status information and, thus, the attaching position and the attachment number are arbitrary.

Output Device 4

The output device 4 is to output the information transmitted from the control unit 6. The output device 4 is installed at a position where the operator who operates the master arm 2 is easy to visually recognize the device. The output device 4 includes at least a display device 41, and may further include a printer, a speaker, a hazard light, etc. The information transmitted from the control unit 6 is outputted and displayed by the display device 41. For example, the speaker outputs the information transmitted from the control unit 6 as sound. Moreover, for example, the printer prints the information transmitted from the control unit 6 on a recording media, such as paper.

Note that, as illustrated in FIG. 1, when one display device 41 is provided as the output device 4 per slave arm 1, each display device 41 may output the status information of the corresponding slave arm 1. In this case, in order for the operator to recognize which slave arm 1 is the operating slave arm 1, the color of the background of the display device 41 where the operating slave arm 1 is displayed may be changed, or an indicating lamp may be provided around the display device 41. Here, "the operating slave arm 1" is an object to be operated by the master device 20, and is the slave arm 1 on which operation is reflected by the operation received by the master device 20.

Storage Device 8

The storage device 8 stores various task programs used for the control of the slave arm 1. The task program may be created as an operation flow for every work. The task program is created, for example, by teaching, and is stored in the storage device 8 so as to be associated with identifying information and task of the slave arm 1. Note that, although the storage device 8 is described independently from the control unit 6, a storage device provided to the control unit 6 may function as the storage device 8.

Moreover, the storage device 8 stores operation sequence information which is created beforehand. The operation sequence information is information related to an operation sequence which defines a series of work processes to be carried out by the slave arm 1 in the workspace. In the operation sequence information, an operating order of the work process is associated with the control mode of the slave arm 1. Moreover, in the operation sequence information, each work process is associated with task program(s) for causing the slave arm 1 to automatically execute the work. Note that the operation sequence information may include the program(s) for causing the slave arm 1 for each work process to automatically execute the work.

Figure 4:
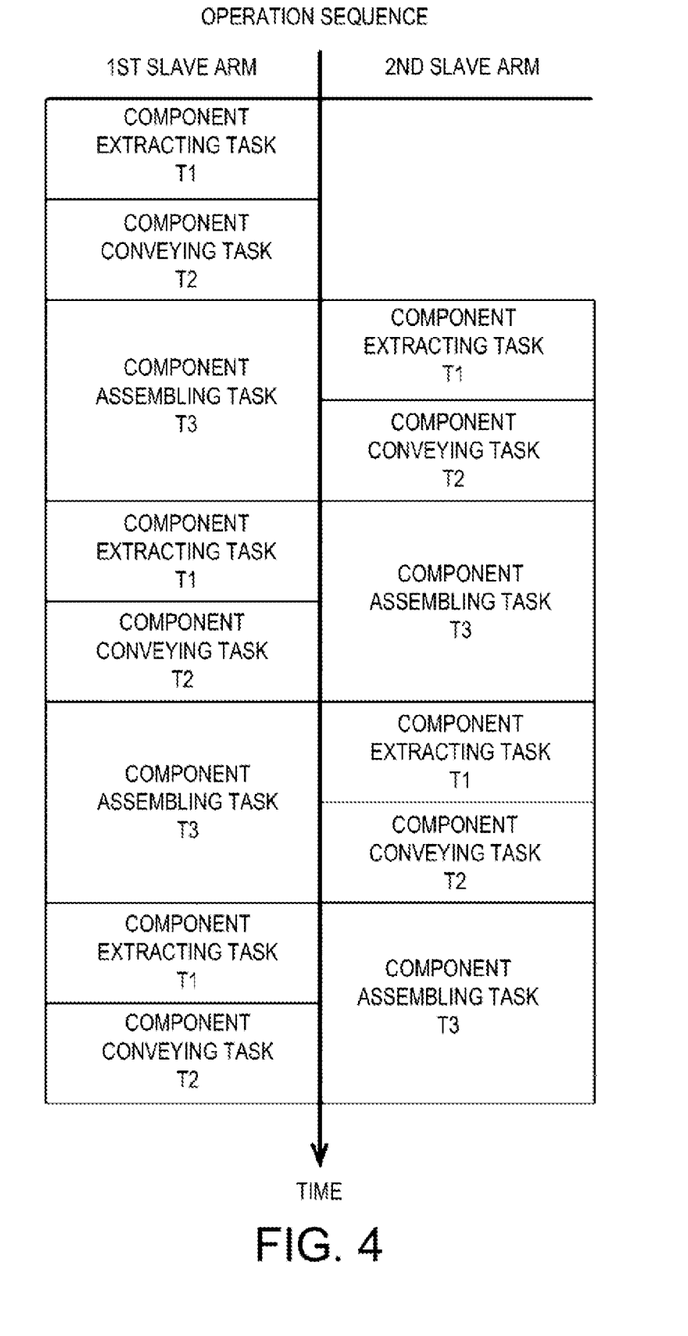
FIG. 4 is a view illustrating one example of operation sequence information.

FIG. 4 illustrates one example of the operation sequence information stored in the storage device 8. Here, the operation sequence of a seat assembling work to an automobile body is described as one example. The operation sequence of the seat assembling work to the automobile body is comprised of a component extracting task T1 in which a seat is taken out from a container, a component conveying task T2 in which the seat is conveyed to near an assembling position of the body, and a component assembling task T3 in which the seat near the assembling position is assembled to the assembling position, and these tasks T1-T3 are repeatedly executed in this order. The component extracting task T1 and the component conveying task T2 among the operation sequence are "automatic parts" in which the slave arm 1 is operated in the automatic mode. The automatic part among the operation sequence is associated with the automatic mode as the control mode. Moreover, the component assembling task T3 among the operation sequence is a "selected part" in which the slave arm 1 operates in the control mode selected from the automatic mode, the manual mode, and the correctable automatic mode. The selected part among the operation sequence is not associated with a specific control mode, and the control mode is selectable.

In FIG. 4, the operation sequence of the first slave arm 1A and the operation sequence of the second slave arm 1B are illustrated in parallel. While the first slave arm 1A executes the component assembling task T3 (i.e., the selected part), the second slave arm 1B executes the component extracting task T1 and the component conveying task T2. Moreover, while the second slave arm 1B executes the component assembling task T3 (i.e., the selected part), the first slave arm 1A executes the component extracting task T1 and the component conveying task T2. Thus, the operation sequence is created so that the selected part appears alternately for the first slave arm 1A and the second slave arm 1B, and the selected part of the first slave arm 1A and the selected part of the second slave arm 1B do not overlap with each other in time.

Control Unit 6

As illustrated in FIG. 2, the plurality of slave arms 1, the master device 20, the output device 4, the status acquiring device 5, the input device 7, and the storage device 8 are communicatably connected to the control unit 6 in a wired or wireless manner.

The control unit 6 is a so-called computer, and has a processor, such as a CPU, and a memory, such as a ROM and/or a RAM (none of them is illustrated). The memory stores control program(s) to be executed by the control unit 6, various fixed data, etc. The processor performs, for example, data transmission and reception with external devices, such as the input device 7, the output device 4, and the storage device 8. Moreover, the processor performs inputs of detection signals from various sensors and outputs of the control signal to each controlled target. In the control unit 6, the processor reads and executes software, such as the program stored in the memory to perform processing for controlling various operation of the system 100. Note that the control unit 6 may execute each processing by a centralized control of a single computer, or may execute each processing by a distributed control of a plurality of collaborating computers. Moreover, the control unit 6 may be comprised of a microcontroller, a programmable logic controller (PLC), etc.

The control unit 6 includes a host controller 60, a plurality of slave controllers 61, the master controller 62, a receiver 63, an output controller 64, and a corrector 65 as functional blocks. Although in FIG. 2 these functional blocks are collectively illustrated as a single control unit 6, each functional block or a combination of two or more functional blocks may be implemented by one or more independent computers. In this case, part of these functional blocks may be arranged in the workspace, and the remainder may be arranged outside the workspace.

The slave controller 61 controls the operation of the slave arm 1. The slave controller 61 includes a first slave controller 61A which controls the operation of the first slave arm 1A, and a second slave controller 61B which controls the operation of the second slave arm 1B. The slave controller 61 may be provided according to the number of slave arms 1 provided to the system 100.

In the automatic mode, the slave controller 61 reads the task program stored in the storage device 8, generates the positional instruction value according to the task program, and gives the positional instruction value, a servo gain, etc. to the motor controller 16 of the slave arm 1. Moreover, in the manual mode, the slave controller 61 generates the positional instruction value based on the operation signal which is accepted by the master arm 2 and received by the receiver 63, and gives the positional instruction value, the servo gain, etc. to the motor controller 16 of the slave arm 1. Moreover, in the correctable automatic mode, the slave controller 61 reads the task program stored in the storage device 8, generates a positional instruction value (or a corrected positional instruction value) based on the task program and a correction instruction value acquired from the corrector 65, and gives the positional instruction value, the servo gain, etc. to the motor controller 16 (see FIG. 3). Note that, in the correctable automatic mode, if the correction instruction value is not given from the corrector 65, the correction instruction value is calculated as zero.

The master controller 62 controls the operation of the master arm 2. The master controller 62 operates the master arm 2 so that the master arm 2 moves or changes in the posture according to an external force applied by the operator to the master arm 2. That is, the operating force of the operator is assisted by the operation of the master arm 2. Moreover, when the operator applies the external force to the master arm 2, the master controller 62 may operate the master arm 2 so that a hand part of the master arm 2 moves along a given route.

Moreover, when the operating slave arm 1 is switched, the master controller 62 automatically changes the posture of the master arm 2 so that the posture of the master arm 2 corresponds to a new posture of the operating slave arm 1. Specifically, when the operating slave arm 1 is switched, the master controller 62 acquires the positional information detected by the position sensor E of each joint JT of the new operating slave arm 1, and operates each joint JTm of the master arm 2 through the motor controller 26 so that the rotational positions of the corresponding joints become substantially equal between the operating slave arm 1 and the master arm 2. Thus, when starting the work in either the manual mode or the correctable automatic mode, the rotational positions of the n-th joint JTn of the operating slave arm 1 and the n-th joint JTmn of the master arm 2 are equal (here, n is an integer from 1 to 6).

The receiver 63 receives the input signal transmitted from the outside of the control unit 6. The input signal received by the receiver 63 may include, for example, a signal transmitted from the master arm 2, a signal transmitted from the input device 7, a signal indicative of the status information transmitted from the status acquiring device 5, etc.

The output controller 64 controls the output device 4 to output to the output device 4 information to be notified the operator. For example, when starting the selected part among the operation sequence, the output device 4 outputs to the display device 41 information for identifying the target slave arm 1, and information for urging the input of selection of the control mode of the slave arm 1. Moreover, for example, when the control modes of the slave arm 1 are the manual mode and the correctable automatic mode, the output device 4 outputs to the display device 41 the status information and an operating status of the slave arm 1 operated by the master arm 2. Moreover, for example, when a failure occurs to the system 100, the output device 4 outputs an alarm to the speaker or the display device 41.

The corrector 65 corrects the motion of the slave arm 1 based on the operation received by the master arm 2, when the control mode of the slave arm 1 is the correctable automatic mode. For example, when the position of the hand part of the master arm 2 changes when the operator moves the master arm 2, the master arm 2 receives the displacement of the hand part as a correcting instruction, and inputs it into the control unit 6. When the receiver 63 receives the correcting instruction signal while the control mode of the slave arm 1 is the correctable automatic mode, the corrector 65 generates a correction instruction value based on the correcting instruction signal. An equation or map by which the correction instruction value is calculated from the correcting instruction signal is stored beforehand. Such a correction instruction value may be a value, for example, proportional to an amount of displacement of the hand part of the master arm 2. The generated correction instruction value is transmitted to the slave controller 61, and the corrected positional instruction value is outputted from the slave controller 61 to the motor controller 16 (see FIG. 3).

The host controller 60 reads the operation sequence information stored in the storage device 8, and outputs instructions to the slave controller 61, the master controller 62, the output controller 64, and the corrector 65 so that the slave arm 1, the master arm 2, the output device 4, and the status acquiring device 5 operate in accordance with the operation sequence information.

Operation of Remote Control Robot System 100

Next, one example of operation of the remote control robot system 100 having the above configuration is described.

The control unit 6 first reads the given operation sequence information stored in the storage device 8, and starts the control of the system 100 in accordance with the operation sequence information.

In accordance with the operation sequence information illustrated in FIG. 4, the control unit 6 first reads and executes the task program of the component extracting task T1 from the storage device 8. Next, the control unit 6 reads and executes the task program of the component conveying task T2. In the component extracting task T1 and the component conveying task T2, the control unit 6 controls the operation of the first slave arm 1A in the automatic mode.

Once the component conveying task T2 is finished, the control unit 6 displays on the display device 41 a selection screen for urging the operator to select the control mode of the subsequent component assembling task T3. In addition, the control unit 6 causes the display device 41 to output the status information of the slave arm 1 for which the control mode is to be selected (here, the first slave arm 1A). Here, the status information which is displayed on and outputted to the display device 41 may include the identifying information of the slave arm 1 which is currently displayed, contents of the process to be performed next, or the like.

The operator visually recognizes the status information of the first slave arm 1A displayed on the display device 41, and selects one of the three control modes. The selection of the control mode by the operator is received by the master device 20 or the input device 7, and is inputted into the control unit 6.

In the above, when the automatic mode is selected, the control unit 6 reads the task program of the component assembling task T3 from the storage device 8, and controls the operation of the first slave arm 1A in the automatic mode. Moreover, when the manual mode is selected, the control unit 6 controls the operation of the first slave arm 1A in the manual mode. Alternatively, when the correctable automatic mode is selected, the control unit 6 controls the operation of the first slave arm 1A in the correctable automatic mode.

In the above, when either one of the manual mode and the correctable automatic mode is selected, the control unit 6 operates the master arm 2 so that the posture of the operating slave arm 1 corresponds to the posture of the master arm 2.

Moreover, in the above, when either one of the manual mode and the correctable automatic mode is selected, the control unit 6 causes the display device 41 to display and output the status information of the operating slave arm 1 throughout the process.

The control unit 6 causes the second slave arm 1B to perform the component extracting task T1 and the component conveying task T2, in parallel with the component assembling task T3 of the first slave arm 1A. Then, once the component assembling task T3 of the first slave arm 1A is finished, and the component extracting task T1 and the component conveying task T2 of the second slave arm 1B are finished, the control unit 6 causes the second slave arm 1B to start the component assembling task T3, and causes the first slave arm 1A to start the component extracting task T1. Thus, the control unit 6 sequentially advances the work process in accordance with the operation sequence.

As described above, the remote control robot system 100 according to this embodiment includes the master device 20 which receives the operator's operation, the plurality of slave arms 1, the storage device 8 which stores the operation sequence information and the task program, and the slave controller 61 (slave control device) which operates the slave arms 1 based on the operation sequence information. Each slave arm 1 has the plurality of control modes of the automatic mode in which the slave arm is operated based on the prestored task program, the manual mode in which the slave arm is operated based on the operator's operation received by the master device 20, and the correctable automatic mode in which the slave arm is operated based on the task program while the operation is sequentially corrected by the operator's operation received by the master device 20. The operation sequence information includes the automatic part in which the slave arm 1 performs a work in the automatic mode, and the selected part in which the slave arm 1 performs a work in the selected one of the plurality of control modes, and the selected parts of the plurality of slave arms are configured so as not to overlap with each other in time. Then, based on the operation sequence information, the control unit 6 operates the slave arm 1 in the automatic mode in the automatic part, and operates the slave arm 1 in the control mode that is selected by the operator from the plurality of control modes for every selected part in the selected part.

Moreover, a method of operating the remote control robot system 100 according to the embodiment described above includes the automatic part in which the slave arm 1 performs a work in the automatic mode, and the selected part in which the slave arm 1 performs a work in one selected from the plurality of control modes. The method includes a step for creating the operation sequence information where the selected parts of the plurality of slave arms 1 do not overlap with each other in time, and a step for causing the slave arm 1 to perform the work based on the operation sequence information, by operating the slave arm 1 in the automatic mode in the automatic part, and operating the slave arm 1 in the control mode that is selected by the operator from the plurality of control modes for every selected part in the selected part.

According to the remote control robot system 100 and the operating method of the same, the operator is able to select the control mode of the slave arm 1 from the automatic mode, the manual mode, and the correctable automatic mode according to the contents of work or the status of the slave arm 1. The selection of the control mode can be performed by the judgment of the operator. For example, works, such as gripping of a vulnerable component, a precision fitting, an accurate positioning or axial alignment, etc. are suitable to be performed in the manual mode or the correctable automatic mode in which the operator's operation is reflectable on the motion of the slave arm 1. In such works, for example, when occurring of a failure is expected if the slave arm 1 is completely operated automatically, the correctable automatic mode may be selected. In the correctable automatic mode, since the automatic operation of the slave arm 1 is used as the basis, and the operation is correctable by the operator's operation, the operator's load is less and a reduction of the work efficiency is suppressed, as compared with the manual mode. Thus, according to the system 100, a nonstop robot system is achieved by the operator selecting the control mode suitable for the status, from the plurality of control modes, for every work.

Moreover, according to the remote control robot system 100 and the operating method of the same, the manual mode and the correctable automatic mode which require the operator's operation do not appear simultaneously in the plurality of slave arms 1. Therefore, a series of work in which the automatic part and the selected part are mixed is efficiently performed using the two or more slave arms 1A and 1B, and the contents of work of the system 100 are extended, as compared with the case where one slave arm is used. That is, the work of the slave arm 1A in the automatic mode, and the work of the slave arm 1B in one of the control modes among the automatic mode, the manual mode, and the correctable automatic mode are simultaneously performed. Moreover, since one operator remotely operates the plurality of slave arms 1, idle times of the slave arm and the operator are shortened. Therefore, an improvement in the work efficiency of the system 100 can be expected.

Moreover, the remote control robot system 100 according to the embodiment includes the master controller 62 (master control device) which acquires, when starting the manual mode or the correctable automatic mode, the rotational position of each joint JT of the operating slave arm 1 among the plurality of slave arms 1, and operates the master arm 2 so that the rotational positions of the corresponding joints JTn and JTmn (n is an integer from 1 to 6) of the master arm 2 and the operating slave arm 1 become equal.

Similarly, in the method of operating the remote control robot system 100 according to the embodiment, the step at which the slave arm 1 performs the work includes receiving, when starting the selected part, a selection of one of the plurality of control modes, and operating the master arm 2, when the received control mode is the manual mode or the correctable automatic mode, so that the rotational positions of the corresponding joints JTn and JTmn (n is an integer from 1 to 6) of the operating slave arm 1 among the plurality of slave arms, and the master arm 2 become equal.

According to the remote control robot system 100 and the operating method of the same, since the rotational positions of the corresponding joints JTn and JTmn of the master arm 2 and the operating slave arm 1 are equal when starting the work in the manual mode or the correctable automatic mode, the operator can learn the status of each joint JT of the operating slave arm 1 by visually recognizing the master arm 2. Therefore, even if the status information of the operating slave arm 1 displayed on the display device 41 does not show the entire operating slave arm 1, the operator can learn the general status of the operating slave arm 1.

Moreover, in the remote control robot system 100 according to the embodiment, the numbers of joints of the plurality of slave arms 1 are equal, the master device 20 is the master arm 2 having the same number of joints as the plurality of slave arms 1, and the link length ratio of the arm part 23 of the master arm 2 differs from the link length ratio of at least one arm part 13 of the slave arm 1.

Thus, the master arm 2 and the slave arm 1 are not limited to have the similarity in their shapes, but the master arm 2 is constructed so as to be easily operable by the operator and the slave arm 1 is constructed so as to be suitable for the contents of work.

Moreover, the remote control robot system 100 according to the embodiment further includes the status acquiring device 5 which acquires the status information of the plurality of slave arms 1, and the output device 4 which outputs the status information of the operating slave arm 1 among the plurality of slave arms 1 when starting the manual mode or the correctable automatic mode.

Thus, the operator is capable of operating the master device 20, while checking the status information of the operating slave arm 1 outputted to the output device 4 (e.g., the display device 41). Note that, in the manual mode, the time required for each work tends to be changed depending on the operator's skill or the difficulty of the work. Therefore, in the manual mode, the output device 4 may be configured to display and output guidance for the manual operation to the operator.

Although the suitable embodiment of the present disclosure is described above, the above configuration may be changed as follows, for example.

For example, in the above embodiment, although the master devices 20 is a robotic arm of a non-similar shape to the slave arm 1, but the form of the master device 20 is not limited to this shape. For example, a robotic arm of a similar shape to the slave arm 1 may be adopted as the master device 20. That is, the master device 20 may be a master arm having the same number of joints as the plurality of slave arms 1, and the link length ratio of the arm part of the master arm may be equal to the link length ratio of at least one arm part 13 of the slave arm 1. Note that, even if the master arm of the similar shape to the slave arm 1 is used as the master device 20, the rotational position of each joint JT of the operating slave arm 1 may be acquired, and the master controller 62 may operate the master arm so that the rotational positions of the corresponding joints become equal between the master arm and the operating slave arm 1, when starting the manual mode or the correctable automatic mode, similar to the above embodiment.

Thus, according the adoption of the robotic arm of the similar shape to the slave arm 1 as the master device 20, the master device 20 takes the corresponding posture to the slave arm 1, and the operator is able to sensuously grasp the posture of the slave arm 1 while looking at the master device 20.

Moreover, in the above embodiment, although the master device 20 is the robotic arm, but the master device 20 is not limited to this structure. For example, the master device 20 may be a horizontal or vertical articulated robot having three or more degrees of freedom, and may be a combination of one or more of known operating means, such as a joy stick, a control lever, an operating button, an operation dial plate, a tablet computer, and a programmable display device (pendant).

It is apparent from the description for a person skilled in the art that many improvements and other embodiments of the present disclosure are possible. Therefore, the above description is to be interpreted only as illustration, and it is provided in order to teach a person skilled in the art the best mode that implements the present disclosure. Details of the structures and/or the functions of the present disclosure may be substantially changed without departing from the spirit of the present disclosure.

DESCRIPTION OF REFERENCE CHARACTERS

1, 1A, 1B: Slave Arm
2: Master Arm
4: Output Device
5: Status Acquiring Device
6: Control Unit
7: Input Device
8: Storage Device
11a-11f: Link
13: Arm Part
15: Pedestal
16: Motor Controller
20: Master Device
21a-21f: Link
23: Arm Part
25: Pedestal
26: Motor Controller
41: Display Device
60: Host Controller
61, 61A, 61B: Slave Controller (Slave Control Device)
62: Master Controller (Master Control Device)
63: Receiver
64: Output Controller
65: Corrector
100: Remote Control Robot System
C1-6, Cm1-6: Current Sensor
E1-6, Em1-6: Position Sensor
JT1-6, JTm1-6: Joint
M1-6, Mm1-6: Drive Motor

What is claimed is:

1. A method of operating a remote control robot system provided with a master device and a plurality of slave arms, each of the plurality of slave arms having a plurality of control modes, the plurality of control modes including
an automatic mode in which the slave arm is operated based on a prestored task program,
a manual mode in which the slave arm is operated based on an operator's operation received by the master device, and
a correctable automatic mode in which the slave arm is operated based on the task program while the operation of the slave arm based on the task program is continuously corrected by an operator's operation received by the master device,
the method comprising:
a step of creating operation sequence information for each of the plurality of slave arms, each of the operation sequence information including
an automatic part in which the slave arm performs a work in the automatic mode, and
a selected part in which the slave arm performs a work in a selected one of the plurality of control modes,
with the proviso that the selected part in each of the operation sequence information for the plurality of slave arms does not overlap with each other in time; and
a step of the plurality of slave arms performing the work based on their respective operation sequence information.

2. The method of claim 1, wherein,
the master device is a master arm having the same number of joints as a first slave arm that is included in the plurality slave arms, and
a step for the first slave arm performing the work includes:
when the first slave arm is starting the selected part in its operation sequence information, receiving a selection selecting one of the plurality of control modes; and
when the selected control mode in the received selection is the manual mode or the correctable automatic mode, operating the master arm so that rotational positions of joints of the first slave arm and rotational positions of corresponding joints of the master arm become equal.

3. A remote control robot system, comprising:
a master device configured to receive an operator's operation;
a plurality of slave arms having a plurality of control modes, the plurality of control modes including
an automatic mode in which the slave arm is operated based on a prestored task program,
a manual mode in which the slave arm is operated based on the operator's operation received by the master device, and
a correctable automatic mode in which the slave arm is operated based on the task program while the operation of the slave arm based on the task program is continuously corrected by the operator's operation received by the master device;
a storage device configured to store operation sequence information for each of the plurality of slave arms, each of the operation sequence information including an automatic part in which the slave arm performs a work in the automatic mode, and a selected part in which the slave arm performs a work in a selected one of the plurality of control modes, with the proviso that the selected part in each of the operation sequence information for the plurality of slave arms does not overlap with each other in time; and a slave control device configured to cause the plurality of slave arms to operate based on their respective operation sequence information.

4. The remote control robot system of claim 3, wherein, the master device is a master arm having the same number of joints as a first slave arm that is included in the plurality of slave arms, and a link length ratio of an arm part of the master arm is equal to a link length ratio of the first slave arm.

5. The remote control robot system of claim 3, wherein, the master device is a master arm having the same number of joints as a second slave arm that is included in the plurality of slave arms, and a link length ratio of an arm part of the master arm differs from a link length ratio of the second slave arm.

6. The remote control robot system of claim 4, comprising a master control device configured to:

when the first slave arm is starting the selected part in its operation sequence information in the manual mode or in the correctable automatic mode, acquire rotational positions of joints of the first slave arm, and operate the master arm such that the acquired rotational positions of the joints of the first slave arm and rotational positions of corresponding joints of the master arm become equal.

7. The remote control robot system of claim 3, further comprising:

a status acquiring device configured to acquire status information of the plurality of slave arms; and an output device configured to output, when one of the plurality of slave arms is starting the selected part in its operation sequence information in the manual mode or in the correctable automatic mode, the status information of an operating slave arm among the plurality of slave arms on which the operation received by the master device is reflected.

8. The remote control robot system of claim 5, comprising a master control device configured to:

when the second slave arm is starting the selected part in its operation sequence information in the manual mode or in the correctable automatic mode, acquire rotational positions of joints of the second slave arm, and operate the master arm such that the acquired rotational positions of the joints of the second slave arm and rotational positions of corresponding joints of the master arm become equal.

* * * * *